United States Patent [19]

Flank et al.

[11] Patent Number: 4,838,865
[45] Date of Patent: Jun. 13, 1989

[54] FLUID MONITOR SYSTEM

[75] Inventors: Hans P. Flank, Malmo; Peter R. Staehr, Lund, both of Sweden

[73] Assignee: Gambro Lundia AB, Sweden

[21] Appl. No.: 898,885

[22] Filed: Aug. 21, 1986

Related U.S. Application Data

[63] Continuation of Ser. No. 625,106, Jun. 27, 1984, abandoned.

[30] Foreign Application Priority Data

Jun. 30, 1983 [SE] Sweden ............................ 03742/83

[51] Int. Cl.⁴ .............................................. A61M 1/03
[52] U.S. Cl. ..................................... 604/118; 73/756; 604/4; 604/65; 128/DIG. 13
[58] Field of Search ......................................... 604/4–6, 604/66, 118, 236, 246, 65, 67, 151, 153; 128/675, 748, DIG. 12, DIG. 13; 73/706, 756

[56] References Cited

U.S. PATENT DOCUMENTS

| | | | |
|---|---|---|---|
| 3,418,853 | 12/1968 | Curtis | 73/730 |
| 3,912,455 | 10/1975 | Lichtenstein | |
| 3,946,731 | 3/1976 | Lichtenstein | |
| 4,227,420 | 10/1980 | Lamadrid | 73/756 |
| 4,398,542 | 8/1983 | Cunningham et al. | 604/118 |
| 4,414,851 | 11/1983 | Maglic | 73/756 |
| 4,454,765 | 6/1984 | Lodge | 73/756 |
| 4,479,760 | 10/1984 | Bilstad et al. | 604/6 |
| 4,490,134 | 12/1984 | Troutner | 604/4 |
| 4,535,635 | 8/1985 | Claren et al. | |

FOREIGN PATENT DOCUMENTS

| | | |
|---|---|---|
| 623134 | of 0000 | Switzerland . |
| 594418 | 9/1977 | Switzerland . |
| 1601855 | 11/1981 | United Kingdom . |
| 2110564A | 6/1983 | United Kingdom . |

*Primary Examiner*—Stephen C. Pellegrino
*Assistant Examiner*—Ralph Lewis
*Attorney, Agent, or Firm*—Lerner, David, Littenberg, Krumholz & Mentlik

[57] ABSTRACT

Systems for monitoring fluids such as blood being treated extracorporeally are disclosed, including a monitor for monitoring the fluid flow through a tube system between a fluid inlet, fluid treatment means and a fluid outlet. The monitor disclosed includes a monitor housing which contains at least one pressure sensor, and a cassette which is adapted to be removably coupled to the monitor housing, the cassette including pressure transmission ducts for transmitting the pressure within the tube system to a pressure transmitting cavity adapted to be juxtaposed with the pressure sensor when the cassette is coupled to the monitor housing so that the pressure within the tube system can be directly measured by the pressure sensor when the cassette is coupled to the monitor housing. In one embodiment of the monitor the cassette includes a portion of the tube system, while in another embodiment a conventional tube system can be affixed to the cassette.

7 Claims, 8 Drawing Sheets

FLUID MONITOR SYSTEM

This is a continuation of application Ser. No. 625,106 filed June 27, 1984, now abandoned.

FIELD OF THE INVENTION

The present invention relates to fluid monitoring systems, and more particularly to systems for monitoring a fluid flowing through tubular conduits between a fluid inlet, fluid treatment means, and a fluid outlet. More particularly, the present invention relates to monitors for monitoring the extracorporeal treatment of blood between a blood inlet, blood treatment means, such as a dialyzer or the like, and a blood outlet. Still more particularly, the present invention relates to such monitors in which tubular conduits conduct the blood from a patient to a treatment unit and back to the patient under the control of the monitor.

More particularly, the present invention relates to monitoring of such a fluid in connection with hemodialysis, hemofiltration, and immunotherapy. It is believed to be apparent, however, particularly to those versed in this art, that the present invention can be applied with considerable advantage to various kinds of extracoporeal blood treatment procedures.

BACKGROUND OF THE INVENTION

In connection with the extracorporeal treatment of fluids such as blood, different types of tube systems are normally used to conduct the blood to and from the patient, to and from the treatement unit, e.g. a dialyzer, and to and from different functional stations, such as stations for pumping, pressure measurement, temperature measurement, sampling, injection, etc. Therefore, after fixing and connecting the tube system to a control monitor, these systems are then connected to the patient, and to the dialyzer or other blood treatment unit. Furthermore, the more functions which are to be included, the more complicated becomes the tube system, as well as the nature of its being affixed to the monitor and connected up therewith.

Attempts have thus been made to integrate at least some of these functions into cassette-like units to be fixed to the dialyzer and/or to the front of the control monitor. Reference in this regard is thus made, for example, to British Patent Nos. 1,601,855 and 1,601,856, U.S. Pat. Nos. 4,211,597 and 4,231,871, and European Patent Application No. 82.420073, published under No. EP 0 069 029.

Another such system for the extracorporeal treatment of blood is shown in British Patent Application No. 2110564A. The device shown therein includes a cassette with tube sections which can be coupled to the device, and which includes external measuring capability such as with respect to flow metering and the like. However, in this device pressure tranducer chamber 29 is stated to be integral with the cassette itself, and is specifically shown in FIG. 5 thereof as being associated with the tubing itself.

The search has therefore continued for improved such extracorporeal monitoring and treatement devices.

SUMMARY OF THE INVENTION

In accordance with the present invention, it has now been discovered that such monitoring devices can be provided, and in particular that this can be done by providing a monitor for monitoring a fluid flowing through conduit means between a fluid inlet, fluid treatment means, and a fluid outlet, and in which the monitor comprises a monitor housing containing at least ome pressure sensing means, and cassette means adapted to be removably coupled to the monitor housing, the cassette means including pressure transmitting means for transmitting the pressure within the conduit means to a pressure transmitting cavity adapted to be juxtaposed with the pressure sensing means when the cassette is coupled to the monitor housing, so that the pressure within the conduit means can be directly measured by the pressure sensing means when the cassette means is coupled to the monitor housing. In a preferred embodiment, the fluid comprises blood, and the fluid treatment means is means for the extracorporeal treatment of the blood, such as dialyzers and the like.

In accordance with a preferred embodiment of the monitor of the present invention, at least a portion of the conduit means comprises tubular conduit means which forms a portion of the cassette means and which is adapted to direct the flow of the fluid between the fluid inlet, the fluid treatment means, and the fluid outlet.

In accordance with a preferred embodiment of the monitor of the present invention, the pressure sensing means comprises a pressure transducer, and preferably a number of pressure transducers are employed in the monitor housing.

In accordance with another embodiment of the monitor of the present invention, the pressure transmitting cavity is bounded by a pressure transmitting surface which is adapted to contact the pressure sensing means when the cassette means is coupled to the monitor housing. In a preferred embodiment, the pressure transmitting surface comprises a flexible wall member, and preferably the monitor housing includes suction means for maintaining the flexible wall member in contact with the pressure sensing means so that the absolute positive or negative pressure in the conduit means can be measured thereby.

In accordance with another embodiment of the monitor of the present invention, the monitor housing includes a source of positive or negative pressure, and the conduit means includes a drip chamber located upstream of the blood outlet, the drip chamber including a lower portion intended to contain a predetermined amount of the fluid such as blood, so as to form a blood level therein, and an upper portion intended to include an air space above the blood level, the cassette means also including connection means for connecting the upper portion of the drip chamber to the source of positive or negative pressure in the monitor housing when the cassette means is coupled to the monitor housing, so that the blood level in the drip chamber can be controlled thereby.

In another embodiment of the monitor of the present invention the conduit means comprises a conventional tube system which can be mounted on the cassette means so that the pressure transmitting means can be connected to selected locations in that conventional tube system. Preferably, the monitor housing also includes a source of positive or negative pressure and the conventional tube system includes a drip chamber. The cassette means can thus include connection means for connecting the upper air space in the drip chamber to the source of pressure in the monitor housing when the cassette has been coupled thereto. In this manner the fluid level in the drip chamber can be controlled.

The system in accordance with a preferred embodiment of the present invention is characterized by the incorporation of tube means in the form of a duct system as part of a substantially rigid cassette, which is adapted to be fixed on, and thus automatically connected to the monitor housing in a manner such that the desired functions, such as the control of pressure, or of other functions of the blood or other fluid, such as temperature, and/or the pumping thereof, are transmitted directly between the monitor and the cassette by merely coupling the latter to the monitor housing.

As indicated above, the monitor preferably comprises one or more pressure transducers which are adapted to be acted upon mechanically by the cassette when the same is fixed to the monitor. For example, the cassette may be adapted so that if presses against the pressure transducer with the help of a flexible wall. Furthermore, by means of suction the flexible wall can be fastened to the pressure transducer for measurement of the absolute positive or negative pressure in the cassette. In this manner, the pressure can be measured without there being any direct contact between the blood and the pressure transducer. Furthermore, no duct connections, such as liquid-tight filters or membranes are required, as is customarily the case in connection with blood pressure measurement in such extracorporeal systems.

The monitor can also include a source of positive and/or negative pressure which is also arranged so that upon fixing the cassette to the monitor housing, it communicates directly with the air space in a drip chamber which is arranged in the cassette, so as to regulate the fluid (blood) level therein. In this manner, excellent safety against air embolisms is achieved. That is, connection of the level regulator takes place automatically, and cannot be forgotten.

The monitor may also include one or more conventional driving elements for one or more tube pumps. The tube segment(s) entering into these pumps preferably consist of segments which are firmly joined to the cassette. In this manner, correct connection of the pump function is facilitated. This ensures that such tube segments are not connected up backwards, which is possible in many conventional tube systems.

The cassette may also comprise one or more expansion chambers. These are required, for example, when the system in accordance with this invention is used for so-called "single-needle" techniques, and the actual treatment unit which is used cannot accommmodate the varying blood volumes which can occur with this technique, where the blood is alternately withdrawn from, and returned to, a patient by means of a single cannula.

It is also possible in accordance with this invention to use the monitor in connection with conventional tube systems by utilizing an adaptor in which the control function of the monitor, such as the pressure sensing means, is arranged to be transmitted to the conventional tube system when it is affixed to the adaptor and the adaptor is coupled to the monitor housing. It is therefore possible to obtain all the advantages of the cassette while still being free to produce, for example, specialized tube systems for specialized fluid treatments.

In this embodiment, the cassette-like holder or adaptor comprises ducts with outlets which are hermetically attachable to the pressure transducer in the monitor housing, which includes means for connection to appropriate pressure measuring positions in the conventional tube system. Coupling of this system to the monitor is thus facilitated.

Moreover, this cassette-like holder may also include an outlet hermetically connectable to a source of positive and/or negative pressure in the monitor housing, which is provided with means for connection to a drip chamber forming a part of the conventional tube system, for regulations of the fluid level in the drip chamber, which can itself be readily affixed to the monitor housing.

Furthermore, the cassette-like holder and/or the monitor housing can also include fastening devices for fixing one or more pump tube segments forming part of a conventional tube system firmly in position relative to one or more tube pump driving elements arranged on the monitor housing.

BRIEF DESCRIPTION OF THE DRAWINGS

Reference is next made to the drawings, for a more complete understanding of the nature of the present invention, and in which:

FIG. 12 is a top, elevational view of another cassette in accordance with the present invention, adapted for blow forming;

FIG. 13 is a side, elevational view of the cassette shown in FIG. 12;

DETAILED DESCRIPTION OF THE INVENTION

The present invention will be more fully understood with reference to FIGS. 1–15, in which like numerals refer to like portions thereof.

The present invention is particularly well suited for application to dialysis. For this reason, and for the sake of simplicity, the particular embodiments which are discussed below are described with reference to dialysis, but it will of course be appreciated that this invention can also be used in connection with other extracorporeal blood treatments.

Figure 1:
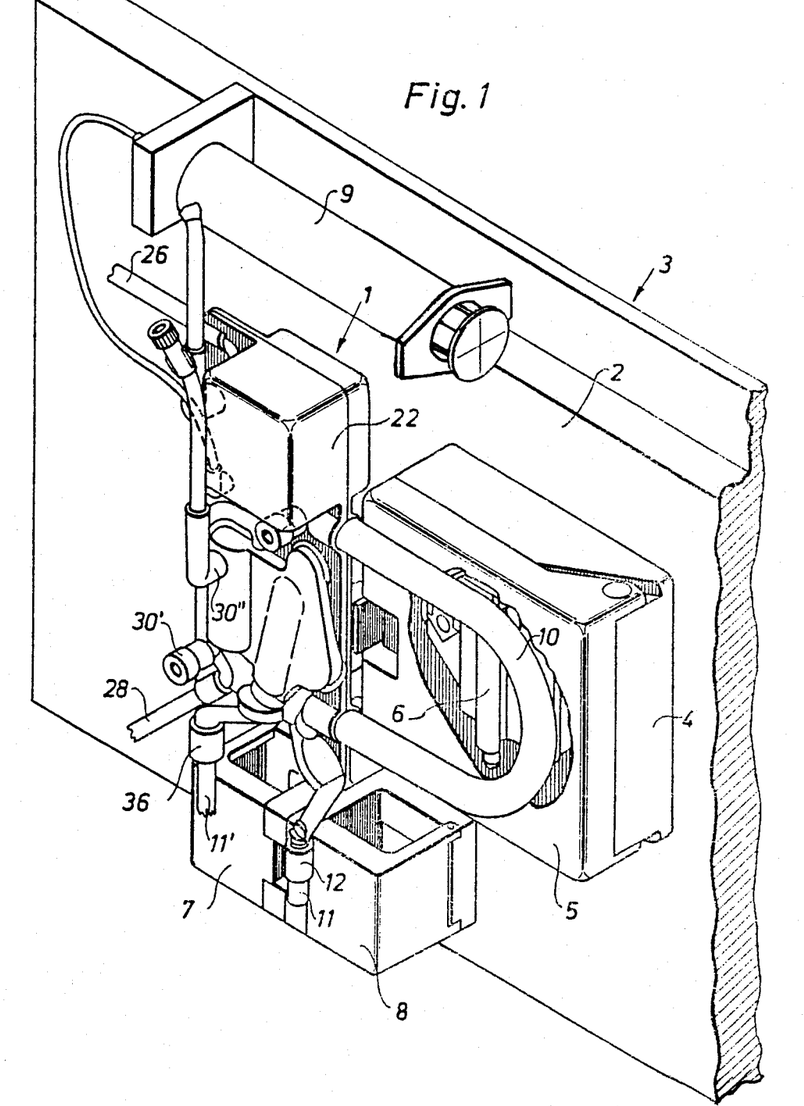
FIG. 1 is a front, elevational, partially sectional view of a portion of a monitor housing and a cassette for affixing thereto in accordance with the present invention.

Referring to FIG. 1, in which a single pump system is shown, a cassette 1 is shown ready to be affixed to the front 2 of a dialysis monitor housing 3. On the outside of the front 2 a tube pump 4 is mounted. Inside the outer door 5 of the pump 4, pump rotor 6 is shown. The front 2 also carries on its outside conventional artery and vein clamps 7 and 8, respectively, and a heparin pump 9. At the back of the cassette various further connecting elements for the transmission of various functions between the cassette and the monitor are included, but these cannot be seen in the figures. Such transmission can, however, take place in both directions.

When the cassette 1 is to be coupled to the housing 3, door 5 is opened so that pump segment 10 can be placed around pump rotor 6. Door 5 is then shut, and it can thus serve as the only fixing element for the cassette 1. It is preferable, however, to provide for further such affixing, either by mechanical means, or by the whole cassette 1 being fastened to front 2 by means of suction. Other components included in cassette 1 will be referred to below, particularly in connection with the description of FIGS. 3, 4 and 12-14.

Figure 2:
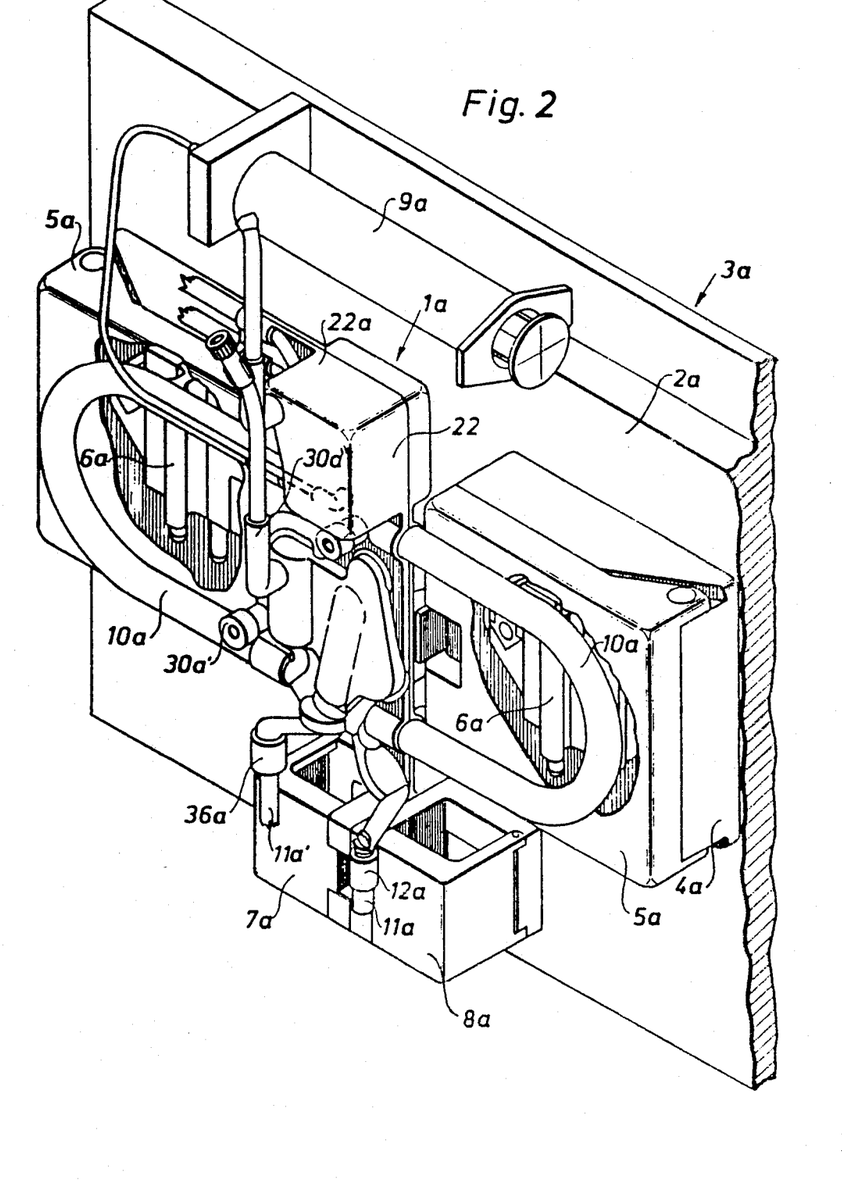
FIG. 2 is a front, elevational, partially sectional view of a portion of a monitor housing and another cassette member for affixing thereto in accordance with the present invention.
Figure 3:
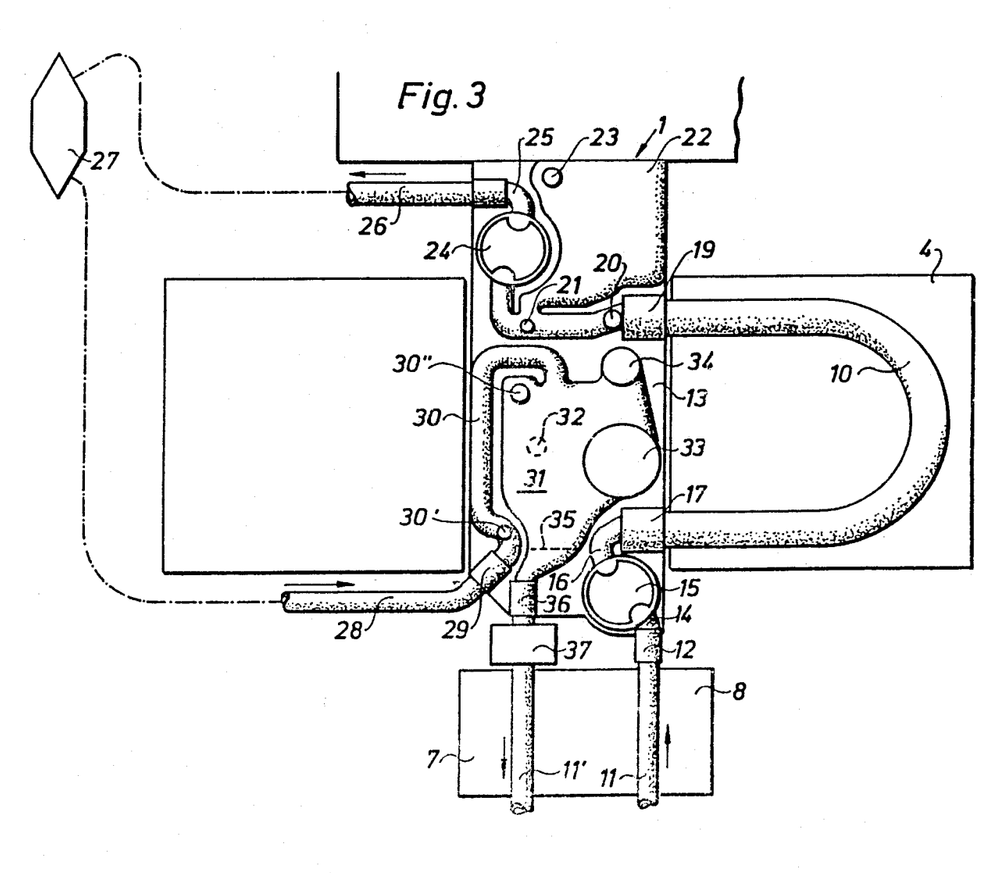
FIG. 3 is a partially schematic, elevational, front view of the flow in accordance with the cassette shown in FIG. 1.

Referring to FIG. 2, in which a double pump system is shown, an alternative embodiment is employed in which the cassette is provided with two pump segments. However, since in principle the construction here is the same as that in FIG. 1, identical reference designations have been used, but in this case including the added letter a. Thus, in FIG. 2 the following components are present:

1a—Cassette with two pump segments
2a—Monitor housing front
3a—Monitor housing
4a—Pump
5a—Pump door
6a—Pump rotor
7a—Vein clamp
8a—Artery clamp
9a—Heparin pump
10a—Pump segments Referring next to FIG. 3, there is shown schematically therein, and slightly modified, the flow diagram which results when the cassette in accordance with FIG. 1 is used. The blood is thus conducted from the patient via tube 11 through artery clamp 8, to the inlet 12 of the central part 13 of the cassette 1. From the inlet 12 the blood passes through a short duct 14 into a first pressure measuring head 15, as described hereinbelow with reference to FIG. 15. The blood is then conducted through duct 16 to the pump inlet 17, from which a pump segment 10 leads to a pump outlet 19. Numeral 20 designates a so-called injection port, which in the present case is intended for the sampling of non-purified blood. Such sampling is carried out by inserting a cannula through a self-closing material, e.g. silicone rubber. Numeral 21 designates a connecting nozzle for a heparin tube (not shown). This connecting nozzle is located directly before the inlet to an expansion chamber 22. The level in the expansion chamber 22 can be regulated by air being sucked out or fed in through a nipple 23. After the blood has passed the expansion chamber 22 it arrives at a second pressure measuring head 24, which may be of the same type as pressure measuring head 15. Thereafter, the blood is conducted through duct 25 out into tube 26, which passes it to a dialyzer 27, indicated symbolically in FIG. 3. From this dialyzer the blood is returned to the central part 13 of cassette 1 through tube 28 and inlet 29. Just prior to inlet 29 there is located another injection port 30' in duct 30, through which the sampling of purified blood can be carried out. The duct 30 opens into a drip chamber 31 with an infusion position 30", a level detecting means 32 such as an ultrasonic detector arranged in the monitor housing, sensing the level through the walls of the cassette 1 and drip chamber 31b, or a light beam and photo cell sensing the level through the walls of the cassette 1 and drip chamber 31b if such walls are formed of transparent material, and a pressure measuring head 33, which once again may be of substantially the same type as pressure measuring head 15. The level detecting means 32 is adapted to control a pump arranged in the monitor housing, which is then connected to a connecting nozzle 34 through which air can be pumped into, or sucked out of, the drip chamber so as to regulate the fluid level therein. In the lower part of the drip chamber a strainer 35 is indicated symbolically just before outlet 36. From outlet 36 the blood first passes an air detector 37, and then vein clamp 7, before being returned to the patient. The level regulating connections 23 and 34 may consist of flexible tubes connected to the nozzles intended for connection to suitable pumps or other sources of pressure. Alternatively, the cassette may be adapted so that these points are tightly pressed directly against suction and/or pressure outlets on the front of the monitor housing.

Figure 4:
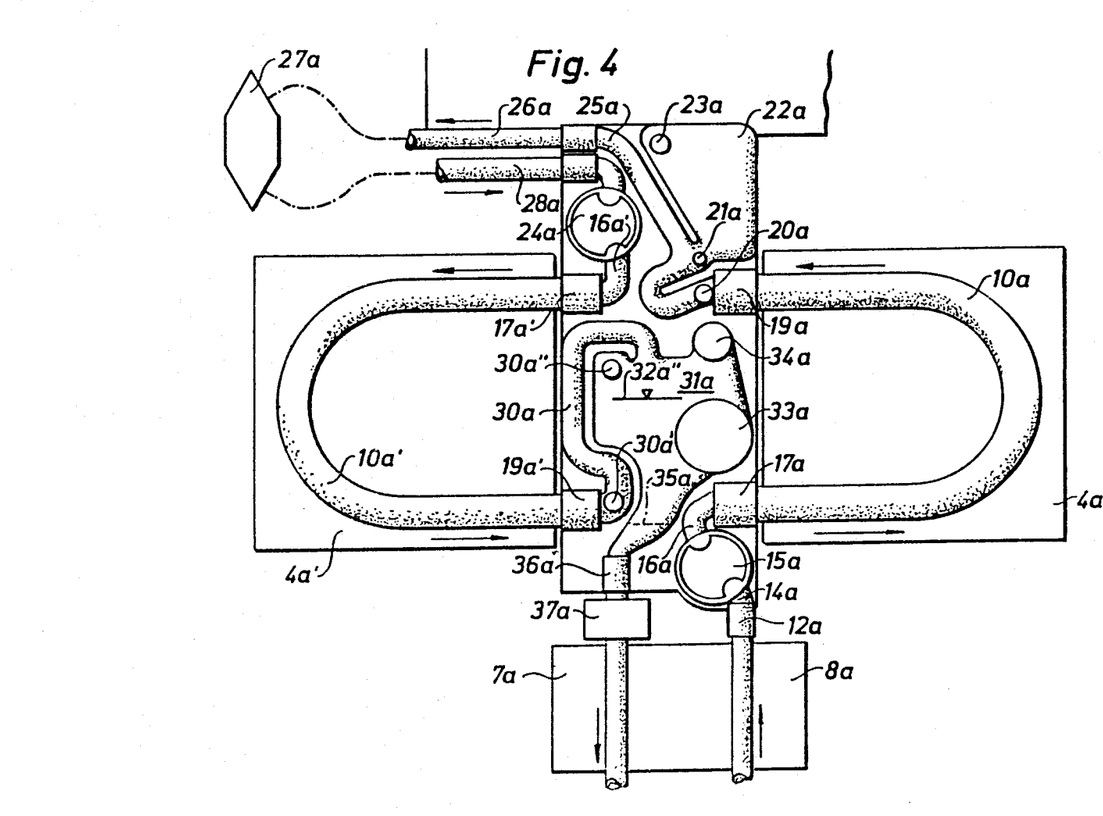
FIG. 4 is a partially schematic, elevational, front view of the flow in accordance with the cassette shown in FIG. 2.

Referring next to FIG. 4, similarly as is the case in connection with FIG. 3, the flow diagram for a cassette is shown which in this case is provided with two pump segments. In principle, the construction here is the same as that in FIG. 3 so that identical reference designations have again been used, but in this case with the adder letter a.

The blood is thus conducted via artery clamp 8a, inlet 12a, duct 14a, pressure measuring head 15a and duct 16a to the inlet 17a of pump 4a. The blood is then conducted through a pump segment 10a, outlet 19a and duct 25a past injection port 20a, and slightly modified expansion chamber 22a, with heparin supply connection 21a and level regulating connection 23a. Without passing any pressure measurement, the blood is then conducted by means of tube 26a to dialyzer 27a, again shown schematically. From there the blood is then conducted through tube 28a to pressure gauge 24a, which has the same position here as the pressure gauge 24, but which in this case measures the outgoing pressure from the dialyzer instead of the incoming pressure. By means of duct 16a', inlet 17a', pump segment 10a' and outlet 19a' the blood is then pumped via duct 30a, which contains an injection port 30a', to a drip chamber 31a, which is constructed essentially in the same manner as the drip chamber 31, that is to say with an infusion position 30a", level detecting means 32a", a pressure measuring head 33a, a connection for level regulation 34a and a strainer 35a. Finally, the blood is again returned to the patient through outlet 36a, air detector 37a and vein clamp 7a.

Figure 5:
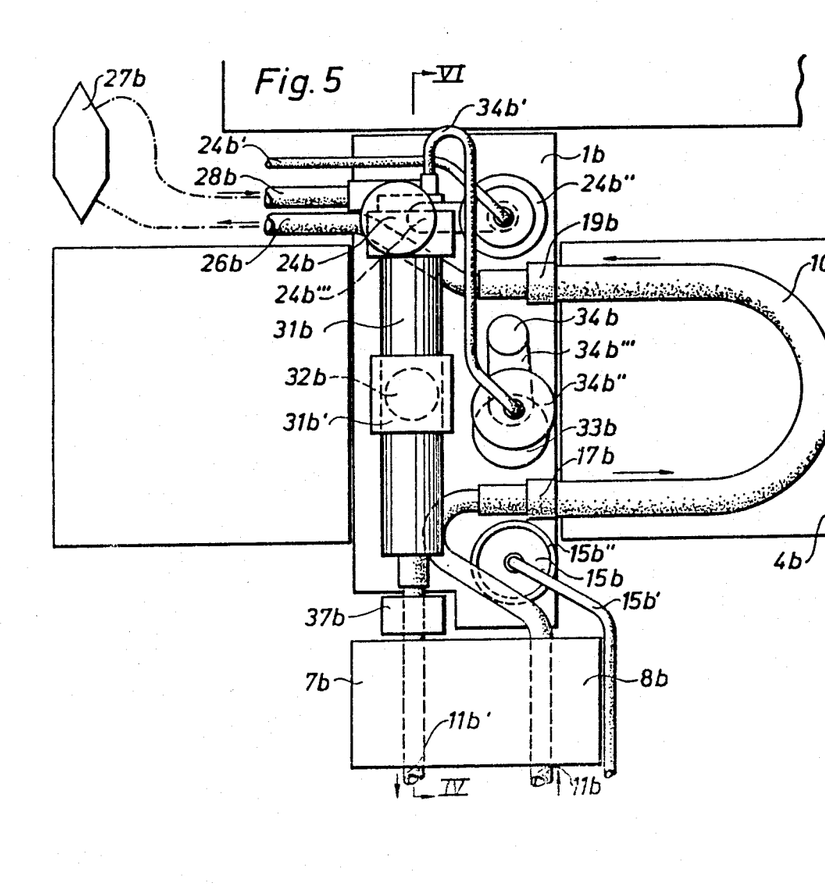
FIG. 5 is a partially schematic, elevational, front view of the flow in accordance with a cassette adapted for a conventional tube set.
Figure 6:
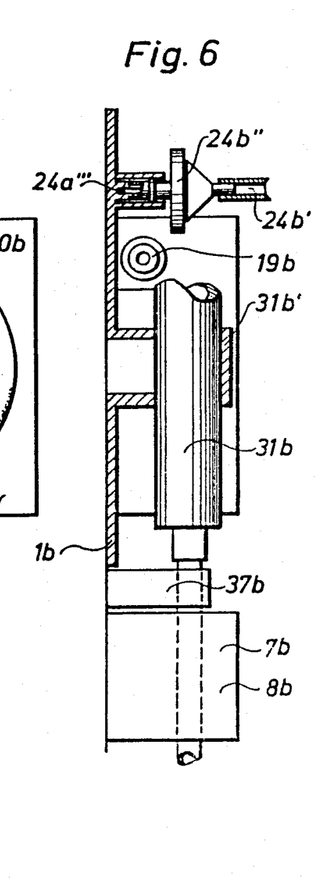
FIG. 6 is a side, elevational, partially sectional view of the cassette shown in FIG. 5.
Figure 7:
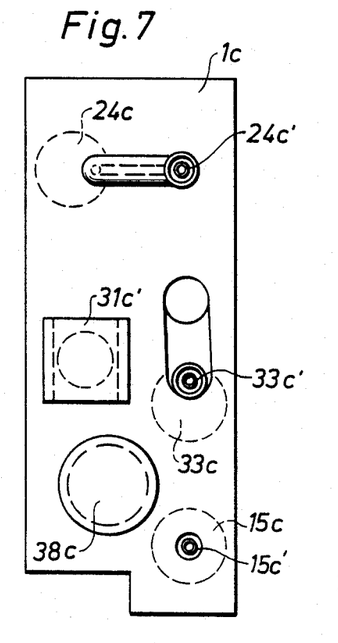
FIG. 7 is a front, elevational, partial view of another cassette in accordance with the present invention.
Figure 8:
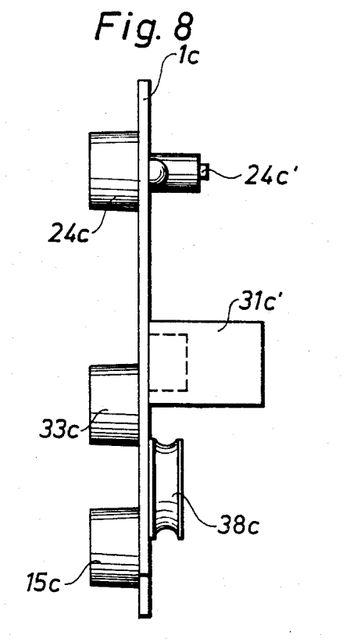
FIG. 8 is a side, elevational view of the cassette shown in FIG. 7.
Figure 9:
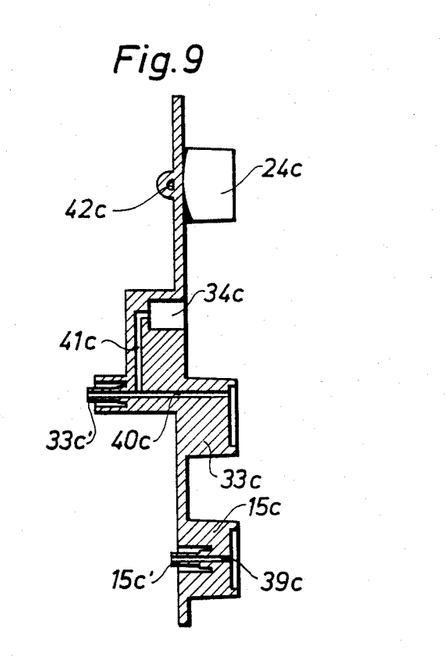
FIG. 9 is a side, elevational, partially sectional view of the cassette shown in FIGS. 7 and 8.
Figure 10:
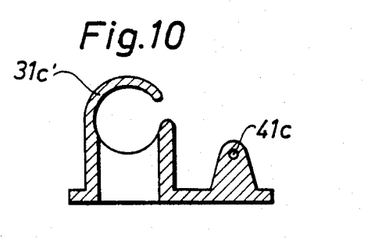
FIG. 10 is a front, elevational, partially sectional view of a portion of the cassette shown in FIGS. 7 and 8.
Figure 11:
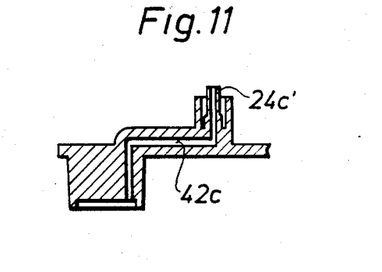
FIG. 11 is a side, elevational, partially sectional view of a portion of the cassette shown in FIGS. 7 and 8.

In order to permit the monitor housing of the present invention to also be used for monitoring conventional tube systems, a special holder adaptor for such systems has been provided in accordance with this invention. Front and sectional views of this holder are shown in FIGS. 5 and 6. Since the function of certain of the components in FIGS. 5 and 6 agrees, at least in principle, with those of corresponding components in FIG. 3, identical reference designations have again been used as much as possible, but in this case with the added letter b. The blood is thus fed to the conventional tube system through duct 11b via artery clamp 8b. With the help of pump 4b, which has an inlet 17b, an outlet 19b and a pump segment 10b, the blood is then pumped through duct 26b to dialyzer 27b, again shown schematically. The blood is then returned through duct 28b to the holder 1b, and more particularly to drip chamber 31b affixed to this holder. The drip chamber is fixed to the holder 1b with the help of a fixing device 31b', which comprises within it a level detecting means 32b. This means, in the same manner as the level detecting means 32 and 32a, is adapted to control a pump aranged in the monitor housing, which by means of level regulating outlet 34b, duct 34b''' and duct 34b' controls the fluid level in the drip chamber by pumping air to and from this chamber. The duct 34b' is also used for transmitting the pressure from the drip chamber 31b to the pressure measuring head 33b for measuring the venous pressure. In the same manner, the arterial pressure is measured with the help of a special pressure measuring head 15b by means of duct 15b', which is connected to duct 11b at a point (not shown) before pump 4b. In the same manner, pressure measuring head 24b is used for measuring the pressure by means of duct 24b' at a point (not shown) either before or after the dialyzer 27b. The tubes 15b', 34b' and 24b' are all connected to respective pressure measuring heads by means of conventional so-called disc filters 15b'', 34b'' and 24b'', respectively. In the latter case, this takes place by means of duct 24b'''.

From the drip chamber 31b the blood then passes through tube 11b' via air dector switch 37b, vein clamp 7b, and back to the patient.

Turning next to FIGS. 7-11, a somewhat modified construction of the holder in accordance with FIGS. 5 and 6 is shown. Again for reasons of simplicity, and for the sake of clarity, in this case the conventional tube system is not shown connected thereto. However, as in principle the construction is the same, identical reference designations have again been used, but in this case with the added letter c. In this case, the three pressure measuring heads are designed 15c, 24c and 33c, and their tube connection positions are designated 15c', 24c' and 33c', respectively. A fixing arrangement 31c' corresponds to fixing arrangement 31b' for drip chamber 31b. To prevent the formation of kinks in the tubes forming the conventional tube system, holder 1c is provided with a guide wheel 38c. Finally, Numerals 39c, 40c, 41c and 42c refer to different ducts which connect the tube connecting positions 15c', 33c' and 24c', respectively, to particular pressure transducers in the monitor housing, and to level regulation outlet 34c, corresponding to outlets 34, 34a and 34b.

Figure 14:
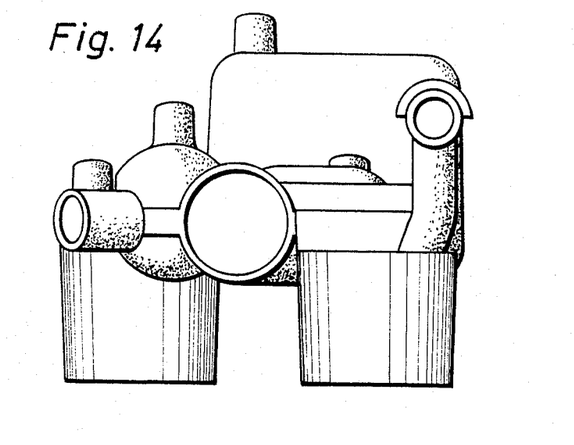
FIG. 14 is a front, elevational view of the cassette shown in FIG. 12.

Referring to FIGS. 12-14, a preferred embodiment of the cassette adapted for one pump segment is shown, in this case for manufacture by means of blow forming. By utilizing this manufacturing process a relatively inexpensive cassette, suitable for throw-away use, can be produced. Alternatively, however, the cassette can also be made, for example, by injection moulding.

This blow-formed version again corresponds in principle with that according to FIGS. 1 and 3. Hence, identical reference designations have again been used, but in this case with the added letter d. The blood is thus fed via inlet 12d, pressure measuring head 15d, duct 16d and pump inlet 17d to the pump (not shown). From the outlet 19d of the pump, the blood is then conducted past injection port 20d and heparin inlet 21d at the inlet to expansion chamber 22d, with its level regulating nipple 23d. Subsequently, the blood is then conducted via pressure measuring head 24d and duct 25d to attachment 25d' for a tube (not shown) intended to be connected to the dialyzer (also not shown).

From the dialyzer, the blood is then returned to a corresponding attachment 29d for another tube which corresponds, for example, to the tube 28 shown in FIG. 3. By means of a line or duct 30d the blood is then led past a sampling position 30d' for the sampling of purified blood. The drip chamber 31d has been given a slightly modified shape in this case so as to include a cylindrical strainer 35d. In the drip chamber an infusion position 31d' is again present, along with a level detecting means 32d, a pressure measuring head 33d and a connection position 34d, intended for level regulation. The function is thus the same as for the cassettes described above. A more detailed description of these functions is therefore not required.

Figure 15:
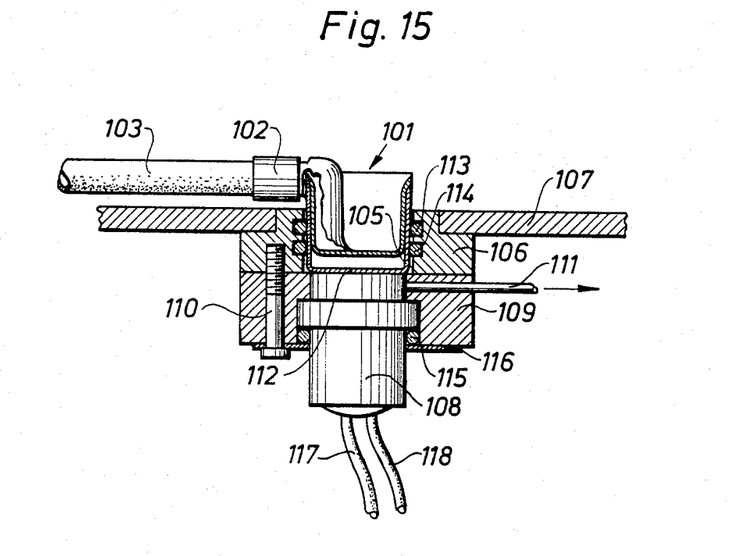
FIG. 15 is a side, elevational, partially sectional view of a portion of a cassette and monitor housing in accordance with the present invention.

In order to illustrate the function of the abovementioned pressure measuring head, reference is made to FIG. 15, which separately shows such a pressure measuring head 101 suck into a machine front 107, which corresponds to the front 2 of the monitor housing 3 shown in FIG. 1. Thus, in FIG. 15 there is shown a container 101 with an inlet 102 which, by means of tube 103 communicates with the medium whose pressure is to be measured. If a through-flowing medium is measured, the container 101 is, of course, also provided with an outlet. In its operating condition, container 101 is sunk into a cavity 105 in a machine component 106, which is fixed into a front plate 107, e.g. the front of a monitor housing for the control of haemodialysis or haemofiltration. On the machine component 106 there is fastened a pressure-sensitive element 108 by means of a further machine component 109. This component may, for example, be screwed on by means of bolt 110. The pressure-sensitive element 108 may, for example, be a piezoelectric pressure pick-up. Alternatively, it may comprise a wire strain pick-up or any other suitable pressure measuring or sensing element. With the help of duct 111 the cavity 105 can thus communicate with a source of vacuum (not shown). In this manner, a pressure-transmitting wall part 112 of container 101 is fastened by suction onto the pressure-sensitive element 108. The pressure-transmitting wall part 112 and the pressure-monitoring surface of the pressure sensitive element 108 are sealed against the surrounding atmosphere with the help of annular seals 113, 114 and 115. The last mentioned seal 115 is thus situated inside a lockwasher 116. Finally, electrical connections to the pressure-sensitive element are indicated by reference Numerals 117 and 118 in FIG. 15.

If, instead, a conventional tube system is to be connected to the monitor by means of pressure-measuring heads of the type shown in FIGS. 5-11, it is thus only necessary for the vacuum duct 111 to be closed before the pressure is measured.

The present invention is not limited to the embodiments described above, but can be varied within the scope of the following claims. In particular, for example, if it is desired to change from the blow forming to the injection moulding process, the shape of the components can be modified substantially. In practice, it has been found that by blow forming, relatively thin bases for the pressure measuring heads can be obtained directly in the actual blowing process. If injection moulding is used, it may become necessary to manufacture the pressure measuring heads with open bases covered by welded-on or glued-on thin membranes.

It will be understood that the embodiment described herein is merely exemplary and that a person skilled in the art may make many variations and modifications without departing from the spirit and scope of the invention. All such modifications and variations are intended to be included within the scope of the invention as defined in the appended claims.

What we claim is:

1. A kit for performing a series of fliud flow monitoring operations comprising:
    (a) a monitor having a housing and fluid condition sensing and control means mounted to said housing in a predetermined pattern;
    (b) a cassette adapted to be removably mounted on said housing at a preselected location, the cassette including permanently connected walls defining a fluid flow path of predetermined configuration and cassette coupling means disposed in a pattern corresponding to said predetermined pattern of said sensing and control means for coupling said fluid condition sensing and control means to said fluid flow path of said cassette when said cassette is mounted at said preselected location on said housing; and
    (c) an adaptor adapted to be removably mounted on said housing at said preselected location instead of said cassette, the adaptor including mounting means for mounting on said adaptor a tube system formed separately from the apaptor and defining a fluid flow path different from said fluid flow path of predetermined configuration defined by said cassette, the adaptor also including adaptor coupling means disposed in a pattern corresponding to said predetermined pattern of said sensing and control means for coupling said fluid sensing and control means to the fluid path of said tube system when said adaptor is mounted at said preselected location on said housing and said tube system is mounted on said adaptor, said monitor having engagement means for mounting either said cassette or said adaptor on said housing at said preselected location so that said monitor can be used sequentially with said cassette and with said adaptor to perform said series of monitoring operations and so that said fluid condition sensing and control means of said monitor may be coupled either to said fluid flow path defined by said cassette when said cassette is mounted on said housing or to the fluid flow path defined by said tube set when said adaptor is mounted on said housing.

2. A kit as claimed in claim 1 wherein said fluid condition sensing and control means includes a pressure transducer, said cassette coupling means includes a pressure transmitting cavity communicating with said fluid flow path of said cassette and having a pressure transmitting wall bearing directly on said pressure transducer when said cassette is mounted on said housing, and said adaptor coupling means includes a pressure transmitting cavity communicating with said fluid flow path of said tube system when said tube system is mounted on said adaptor and having a pressure transmitting wall bearing directly on said pressure transducer when said adaptor is mounted on said housing.

3. A kit as claimed in claim 1 wherein said fluid flow path of said cassette includes a drip chamber, said fluid condition sensing and control means includes a source of positive and/or negative air pressure, said cassette coupling means includes a cassette port communicating with said drip chamber, said cassette port being connected to said pressure source when said cassette is mounted on said housing, and said adaptor coupling means includes an adaptor port, said adaptor port being connected to said pressure source when said adaptor is mounted on the housing, said adaptor connecting means including drip chamber connecting means for connecting said adaptor port to a drip chamber formed separately from said adaptor.

4. A kit as claimed in claim 3 wherein said fluid condition sensing and control means includes level detecting means, said drip chamber of said cassette being juxtaposed with said level detecting means when said cassette is mounted on said housing, said adaptor including means for retaining a separately formed drip chamber in juxtaposition with said level detecting means when said adaptor is mounted on said housing.

5. A kit as claimed in claim 1 wherein said cassette includes an expansion chamber communicating with the fluid path of said cassette.

6. A kit as claimed in claim 1 wherein said monitor includes a pump drive, said cassette including a tube defining a portion of the fluid path of the cassette, said tube being engaged with said pump drive when the cassette is mounted on said housing.

7. A kit for performing a series of fluid flow monitoring operations comprising:
    (a) a monitor having a housing and fluid condition sensing and control means mounted to said housing in a predetermined pattern;
    (b) a cassette adapted to be removably mounted on said housing at a preselected location, the cassette including permanently connected walls defining a fluid flow path of predetermined configuration and cassette coupling means disposed in a pattern corresponding to said predetermined pattern of said sensing and control means for coupling said fluid condition sensing and control means to said fluid flow path of said cassette when said cassette is mounted at said preselected location on said housing; and
    (c) an adaptor adapted to be removably mounted on said housing at said preselected location, the adaptor including mounting means for mounting on said adaptor a tube system formed separately from the adaptor and definding a fluid flow path, the adaptor also including adaptor coupling means disposed in a pattern corresponding to said predetermined pattern of said sensing and control means for coupling said fluid sensing and control means to the fluid path of said tube system when said adaptor is mounted at said preselected location on said housing and said tube system is mounted on said adaptor, said monitor having engagement means for mounting either said cassette or said adaptor on said housing at said preselected location so that said monitor can be used sequentially with said cassette and with said adaptor to perform said series of monitoring operations and so that said fluid condition sensing and control means of said monitor may be coupled either to said fluid flow path defined by said cassette when said cassette is mounted on said housing or to the fluid flow path defined by said tube set when said adaptor is mounted on said housing;

said fluid condition sensing and control means including a pressure transducer, said cassette coupling means including a pressure transmitting cavity communicating with said fluid flow path of said cassette and having a pressure transmitting wall bearing directly on said pressure transducer when said cassette is mounted on said housing, and said adaptor coupling means including a pressure transmitting cavity communicating with said fluid flow path of said tube system when said tube system is mounted on said adaptor and having a pressure transmitting wall bearing directly on said pressure transducer when said adaptor is mounted on said housing, said monitor including suction means for applying suction around said pressure transducer to maintain said pressure transmitting wall of said cassette coupling means or said adaptor coupling means in contact with said pressure transducer.

* * * * *